(12) United States Patent
Poo et al.

(10) Patent No.: US 8,986,330 B2
(45) Date of Patent: Mar. 24, 2015

(54) AORTIC CROSS CLAMP

(71) Applicant: Miami Instruments LLC, Surfside, FL (US)

(72) Inventors: Ramon Poo, Miami, FL (US); Joseph Lamelas, Miami, FL (US)

(73) Assignee: Miami Instruments LLC, Surfside, FL (US)

( * ) Notice: Subject to any disclaimer, the term of this patent is extended or adjusted under 35 U.S.C. 154(b) by 0 days.

(21) Appl. No.: 13/940,639

(22) Filed: Jul. 12, 2013

(65) Prior Publication Data

US 2015/0018856 A1 Jan. 15, 2015

(51) Int. Cl.
  *A61B 17/08* (2006.01)
  *A61B 17/122* (2006.01)
  *A61B 17/128* (2006.01)

(52) U.S. Cl.
  CPC .......... *A61B 17/122* (2013.01); *A61B 17/128* (2013.01)
  USPC ............................................. 606/158

(58) Field of Classification Search
  CPC .......................... A61B 17/122; A61B 17/128
  USPC .................... 606/205, 207, 157, 158
  See application file for complete search history.

(56) References Cited

U.S. PATENT DOCUMENTS

| | | | |
|---|---|---|---|
| 3,378,010 A | | 4/1968 | Codling |
| 4,444,187 A | | 4/1984 | Perlin |
| 4,605,002 A | * | 8/1986 | Rebuffat .................. 606/148 |
| 4,777,949 A | | 10/1988 | Perlin |
| 5,030,226 A | | 7/1991 | Green et al. |
| 5,197,970 A | | 3/1993 | Green et al. |
| 5,282,806 A | * | 2/1994 | Haber et al. ................. 606/139 |
| 5,415,666 A | | 5/1995 | Gourlay et al. |
| 5,425,743 A | * | 6/1995 | Nicholas ................... 606/208 |
| 5,490,819 A | * | 2/1996 | Nicholas et al. ............. 600/201 |
| 5,514,147 A | | 5/1996 | Hoskin et al. |
| 5,522,830 A | * | 6/1996 | Aranyi ..................... 606/174 |
| 5,527,339 A | * | 6/1996 | Koscher et al. ............. 606/205 |
| 5,569,274 A | | 10/1996 | Rapacki et al. |
| 5,593,414 A | | 1/1997 | Shipp et al. |
| 5,601,573 A | | 2/1997 | Fogelberg et al. |
| 5,713,919 A | * | 2/1998 | Lahr ........................ 606/207 |
| 5,728,121 A | * | 3/1998 | Bimbo et al. ................ 606/207 |
| 5,752,973 A | * | 5/1998 | Kieturakis ................. 606/207 |
| 5,921,996 A | | 7/1999 | Sherman |

(Continued)

FOREIGN PATENT DOCUMENTS

EP 2042112 4/2009

OTHER PUBLICATIONS

European Search Report mailed on Dec. 4, 2014 in EP Application No. 14170735.6. (7 pages).

*Primary Examiner* — Elizabeth Houston
*Assistant Examiner* — Todd J Scherbel
(74) *Attorney, Agent, or Firm* — Novak Druce Connolly Bove + Quigg LLP

(57) ABSTRACT

An aortic cross clamp includes an elongated handle and a clamp head. The clamp head has opposing jaws having open and closed positions. At least one of the jaws is pivotally mounted to a jaw actuator so as to be pivotal relative to the opposing jaw and about an axis distanced from the opposing jaw. A locking mechanism is provided for locking the jaws in the closed position. A jaw drive mechanism is operable through the elongated handle for moving the jaws between the open and closed positions. A method of clamping the aorta is also disclosed.

18 Claims, 15 Drawing Sheets

(56) References Cited

U.S. PATENT DOCUMENTS

| | | | |
|---|---|---|---|
| 6,139,563 A * | 10/2000 | Cosgrove et al. | 606/205 |
| 6,280,184 B1 * | 8/2001 | Hamilton | 433/4 |
| 6,610,074 B2 | 8/2003 | Santilli | |
| 6,723,109 B2 | 4/2004 | Solingen | |
| 6,808,491 B2 | 10/2004 | Kortenbach et al. | |
| 6,896,684 B2 | 5/2005 | Monassevitch et al. | |
| D583,941 S * | 12/2008 | Leroy | D24/135 |
| 2001/0049540 A1 | 12/2001 | Santilli | |
| 2005/0090838 A1 | 4/2005 | Sixto et al. | |
| 2005/0119677 A1 | 6/2005 | Shipp | |
| 2005/0251183 A1 | 11/2005 | Buckman et al. | |
| 2005/0277958 A1 | 12/2005 | Levinson | |
| 2006/0100649 A1 | 5/2006 | Hart | |
| 2006/0259049 A1 | 11/2006 | Harada et al. | |
| 2008/0234725 A1 * | 9/2008 | Griffiths et al. | 606/208 |
| 2010/0268254 A1 | 10/2010 | Golden et al. | |
| 2011/0009899 A1 * | 1/2011 | Picha Muthu et al. | 606/207 |
| 2011/0301606 A1 * | 12/2011 | Kerr | 606/52 |
| 2012/0022584 A1 | 1/2012 | Donnigan et al. | |

* cited by examiner

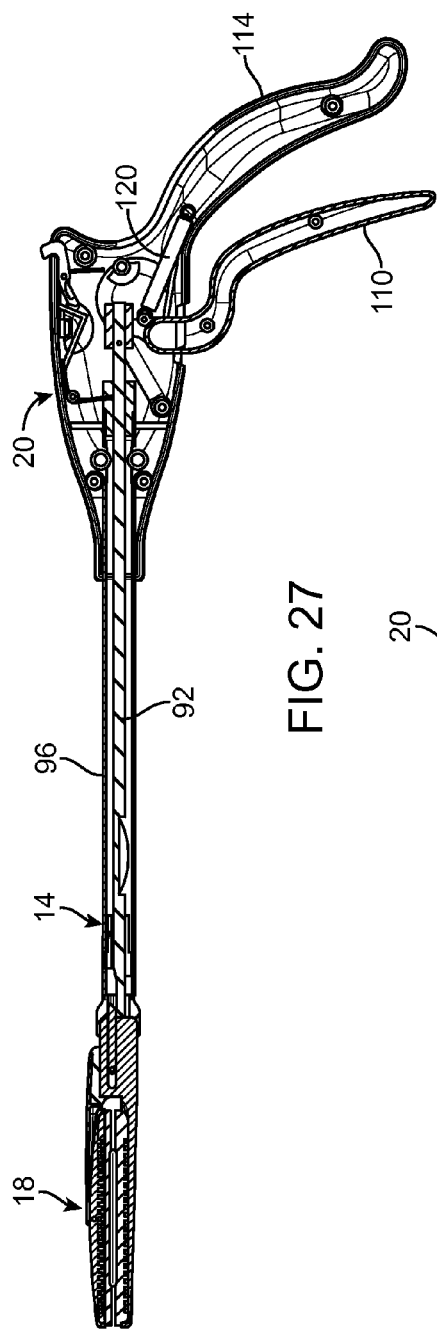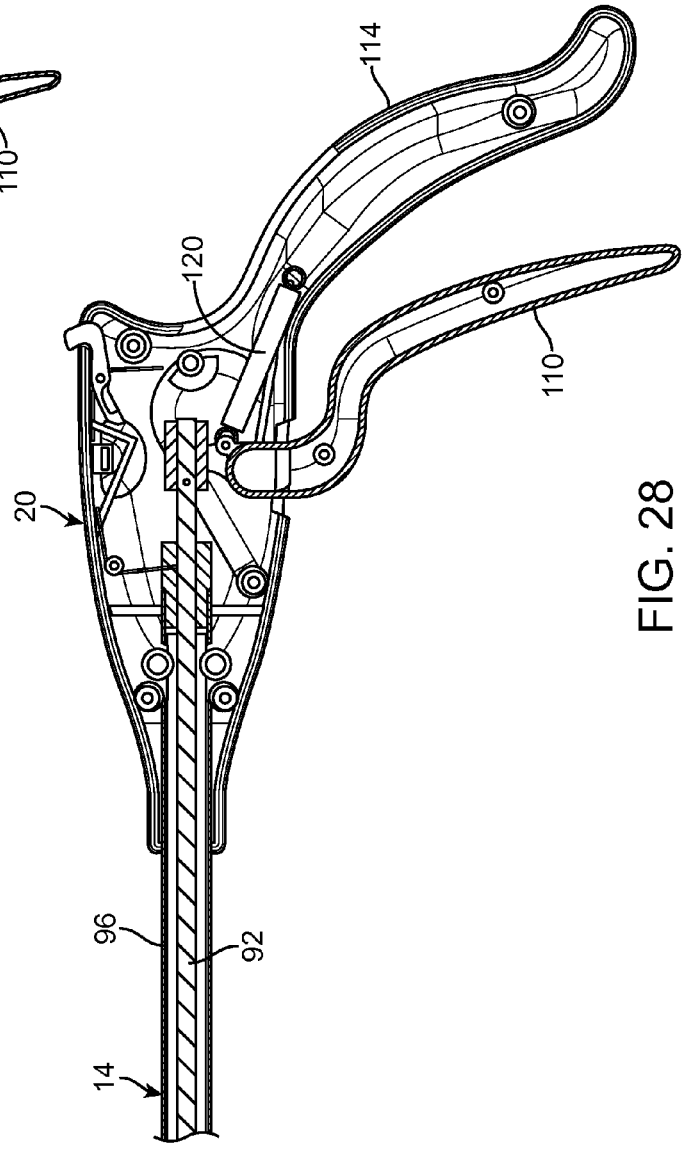

AORTIC CROSS CLAMP

FIELD OF THE INVENTION

This invention relates to cross clamps, and more particularly to aortic cross clamps.

BACKGROUND OF THE INVENTION

Cross clamps are used in heart surgery to clamp the aorta. Increasingly, minimally invasive techniques have made traditional cross clamps less desirable. There is a need for aortic cross clamps which are suited for minimally invasive surgical techniques, either applied through a port or cannula or through a small incision.

SUMMARY OF THE INVENTION

An aortic cross clamp includes an elongated handle and a clamp head. The clamp head has opposing jaws having open and closed positions. At least one of the jaws is pivotally mounted to a jaw actuator so as to be pivotal relative to the opposing jaw and about an axis distanced from the opposing jaw. A locking mechanism is provided for locking the jaws in the closed position. A jaw drive mechanism is operable through the elongated handle for moving the jaws between the open and closed positions.

The locking mechanism can be provided in the jaw. The locking mechanism can comprise a cam and a cam follower. The cam can be curved and can provide a mechanical advantage of between 1 and 20 or any mechanical advantage between 1 and 20.

The clamp head can have a long axis and the cam can have first and second cam portions. The first cam portion can make an angle of between 1-89 with the long axis and the second cam portion can make an angle of between 1-20 with the long axis.

The cam follower can be connected to a cam shaft. The jaw drive mechanism can comprise a jaw drive shaft in the elongated handle. The cam shaft is connectable to cooperating structure on the jaw drive shaft to move the jaws between the open and closed positions. The cam shaft has a proximal end and a distal end, and the distal end can be connected to the cam follower. The proximal end can have structure for detachably engaging the jaw drive shaft.

The elongated handle can comprise a tubular housing, and the jaw drive shaft can be provided within the housing. The elongated handle can be attached to a handle grip housing. The jaw drive mechanism can further comprise a jaw drive cam follower connected to the jaw drive shaft, and a jaw drive cam can be pivotally mounted to the handle grip housing. Movement of the jaw drive cam causes movement of the jaw drive cam follower and the jaw drive shaft so as to move the jaw drive shaft proximally or distally and move the jaws between the open and closed positions.

A trigger can be provided for causing movement of the jaw drive cam. A biasing can be provided for the trigger and a ratchet mechanism can be provided for securing the trigger in a position against the action of the biasing.

The clamp head and the elongated handle can have cooperating engagement structure for detachably engaging the clamp head to the handle. The cooperating engagement structure can comprise opposing graspers pivotally mounted to the elongated handle. The graspers can be biased to an open position and a grasper drive member can be operable to move the graspers against the biasing to a closed position. The grasper drive member can be a tubular housing. A grasper actuating lever can be provided. Movement of the grasper actuating lever is operable to move the grasper drive member and the graspers between the open and closed positions.

The jaws can comprise flexible engagement pads for reducing trauma to the aorta when clamped by the jaws. The flexible engagement pads can be secured to the any suitable method.

A method of clamping the aorta includes the steps of providing an aortic cross clamp having an elongated handle, a clamp head, the clamp head having opposing jaws having open and closed positions, at least one of the jaws being pivotally mounted to a jaw actuator so as to be pivotal relative to the opposing jaw and about an axis distanced from the opposing jaw, and a locking mechanism for locking the jaws in the closed position, and a jaw drive mechanism operable through the elongated handle for moving the jaws between the open and closed positions. The method further includes the step of closing the jaws about an aorta while permitting the pivotally mounted jaw to pivot upon contact with the aorta. The method can also comprise the step of detaching the clamp head from the handle after the jaws have been closed about the aorta.

BRIEF DESCRIPTION OF THE DRAWINGS

There are shown in the drawings embodiments that are presently preferred it being understood that the invention is not limited to the arrangements and instrumentalities shown, wherein:

FIG. 27 is a cross-section of an aortic cross clamp in a closed position.

FIG. 28 is an enlarged cross-section of a handle grip assembly.

DETAILED DESCRIPTION OF THE INVENTION

Figure 1:
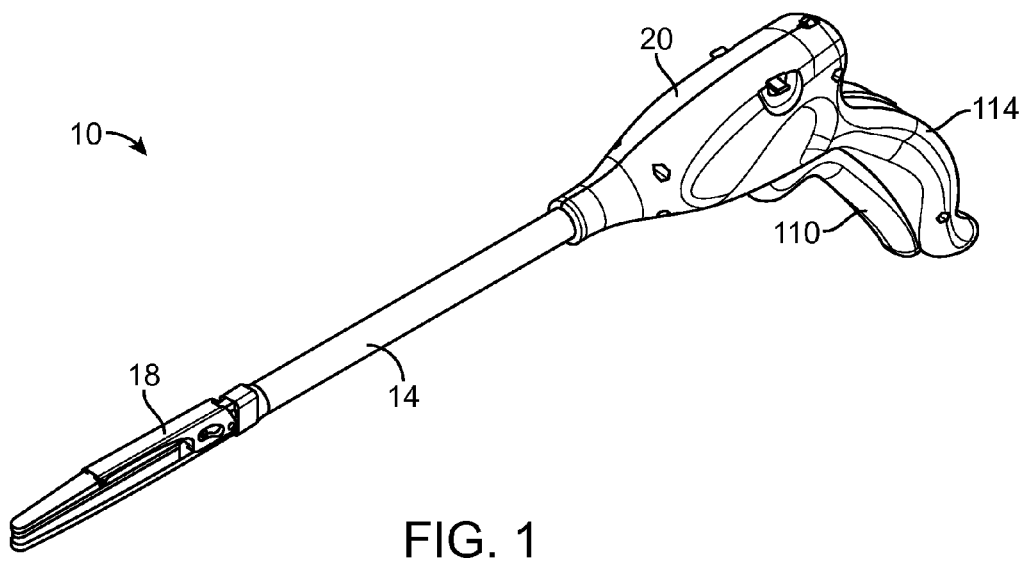
FIG. 1 is a perspective view of an aortic cross clamp according to the invention in a closed position.
Figure 2:
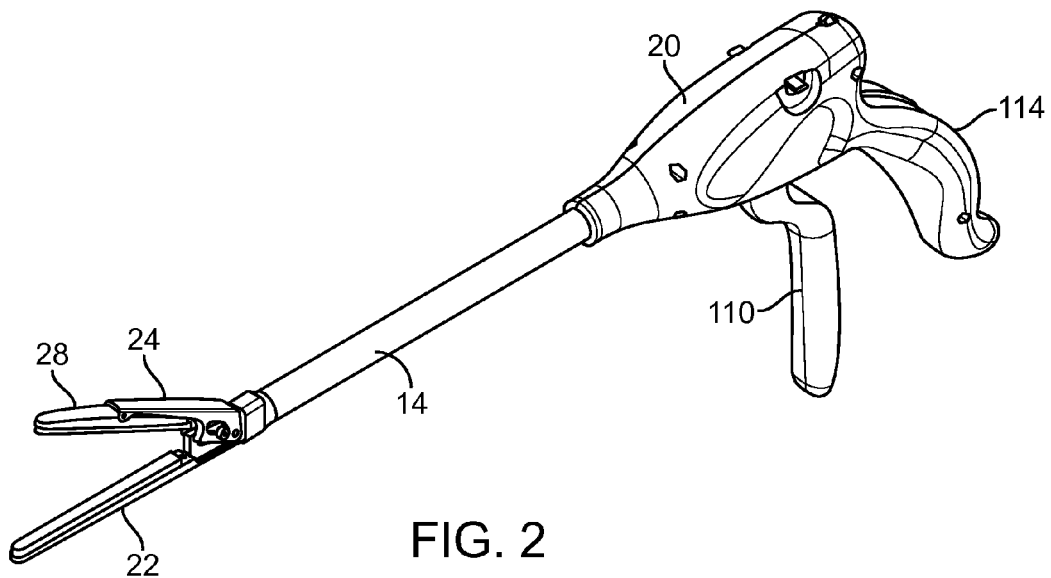
FIG. 2 is a perspective view in an open position.
Figure 3:
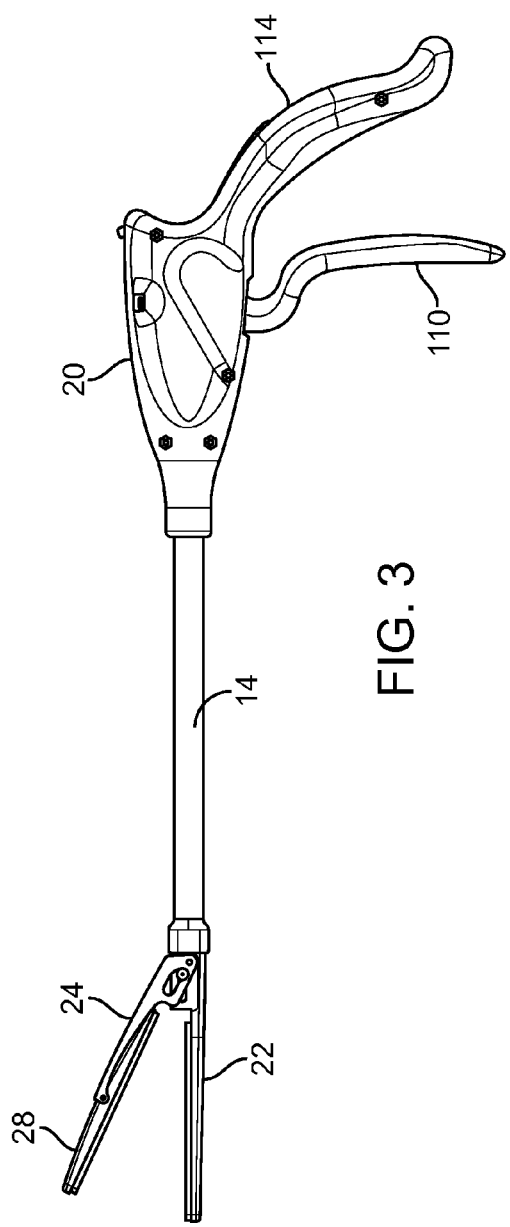
FIG. 3 is a side elevation in an open position.
Figure 4:
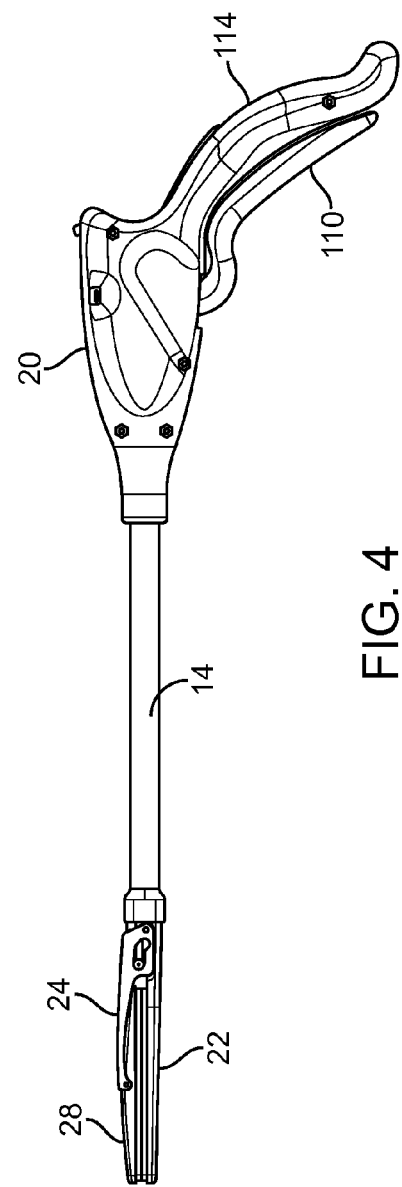
FIG. 4 is a side elevation in a closed position.

There is shown in the drawings an aortic cross clamp 10 according to one embodiment of the invention. The aortic cross clamp 10 includes an elongated handle 14 and a clamp head 18. The clamp head 18 has opposing jaws 22 and 28 having open and closed positions. At least one of the jaws is pivotally mounted to a jaw actuator 24 so as to be pivotal relative to the opposing jaw and about an axis distanced from the opposing jaw. This axis is also substantially transverse to the long dimension of the jaws. A locking mechanism is provided for locking the jaws in the closed position. A jaw drive mechanism is operable through the elongated handle 14 for moving the jaws between open and closed positions. In one embodiment the elongated handle 14 is connected to a handle grip 20.

The jaw 28 can be pivotally mounted to jaw actuator 24 by any suitable structure, such as a pivot pin 30. The pivot pin 30 permits rotation about the axis distanced from the opposing jaw 22. In this manner, the jaw 28 will engage the aorta in a manner in which more even pressure is distributed across the surface of the aorta, and without pinching or scissoring which can potentially cause injury to the aorta. In one aspect the axis is within 85-95° relative to the long axis of the jaws. The range of motion of the pivoting jaw can be varied, and in one embodiment is between 0 and 20 degrees or any range of motion between 0 and 20 degrees. A range of motion that is larger than 20 degrees is also possible. Other mechanisms for pivotally mounting the jaw 28 to the jaw actuator 24 are possible. The jaws can be covered by flexible pads 32 and 36 to further protect the aorta against damage. In another aspect the jaw actuator 24 is pivotally mounted to the clamp head 18 about a pivot pin 52 or other suitable structure.

Figure 23:
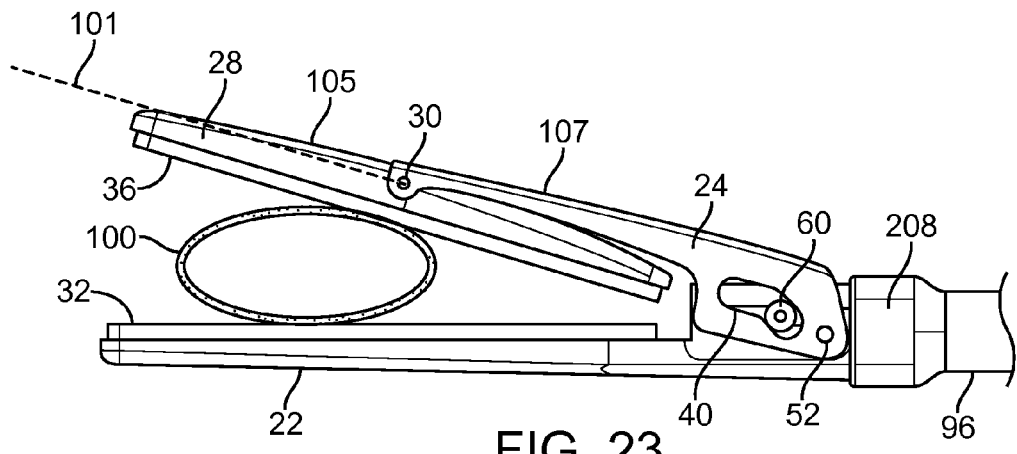
FIG. 23 is a side elevation of an aorta positioned in a clamp head in an open position.
Figure 24:
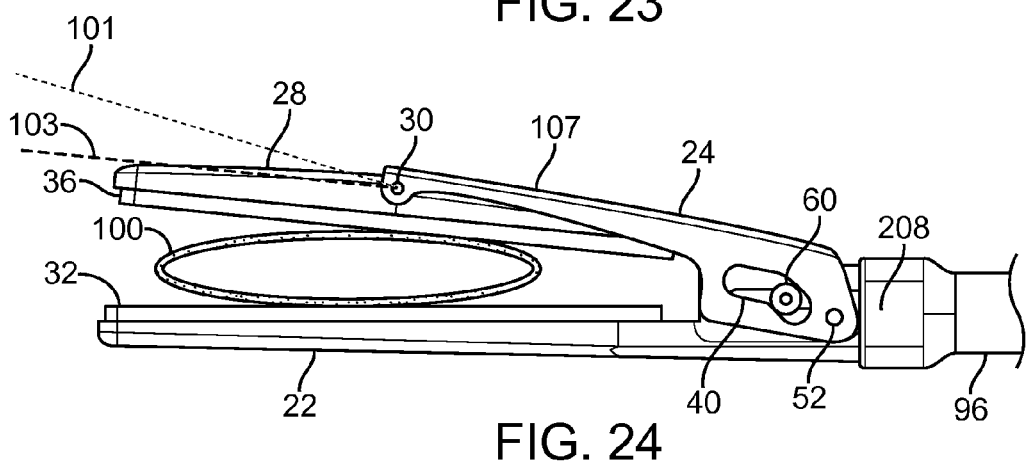
FIG. 24 is a side elevation of an aorta positioned in a clamp head in a first intermediate position.
Figure 25:
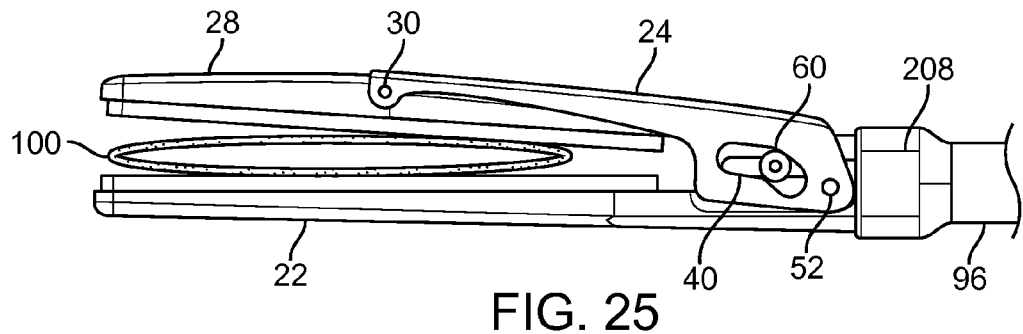
FIG. 25 is a side elevation of an aorta positioned in a clamp head in a second intermediate position.
Figure 26:
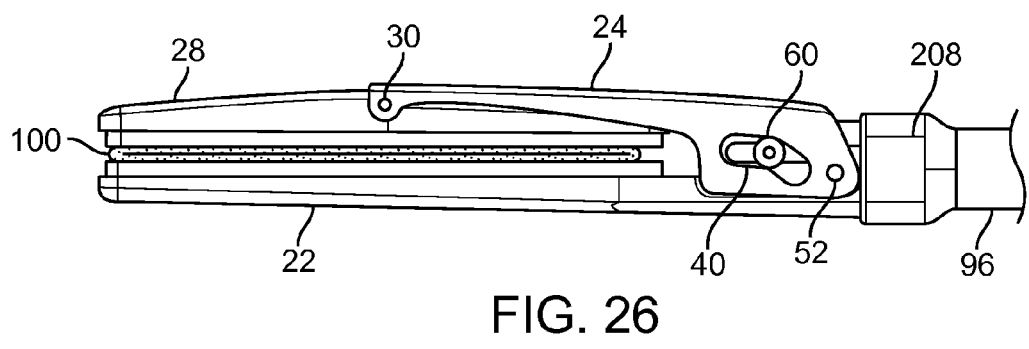
FIG. 26 is a side elevation of an aorta positioned in a clamp head in a closed position.

The action of the pivoting jaw is illustrated in FIGS. 23-26. Upon closing of the jaws 22 and 28, the aorta 100 will be initially contacted (FIG. 23). The jaw 28 will have an initial axis 101 relative to an axis of the jaw actuator 24 such as that defined by top surface 107 of the actuator 24. The top surface 105 of the jaw 28 can be convex to facilitate pivoting of the jaw 28 relative to the actuator 24. Upon further closing of the jaws 22 and 28 (FIG. 24), the aorta 101 will be compressed and will have a new axis 103. The axis 103 of the jaw 28 in this position will have an increased angle relative to the surface 107 of the jaw actuator 24. This pivoting of the jaw 28 will cause the jaw 28 to be substantially more parallel relative to the jaw 22 than if pivoting were not possible. This will create a more even pressure on the aorta 100 during compression and avoid or reduce pinching or scissoring of the aorta 100. Further closing of the jaws 22 and 28 will substantially compress the aorta 100 (FIG. 25) until the closed position is attained (FIG. 26) where the jaws 22 and 28 can be substantially parallel to one another.

Figure 11:
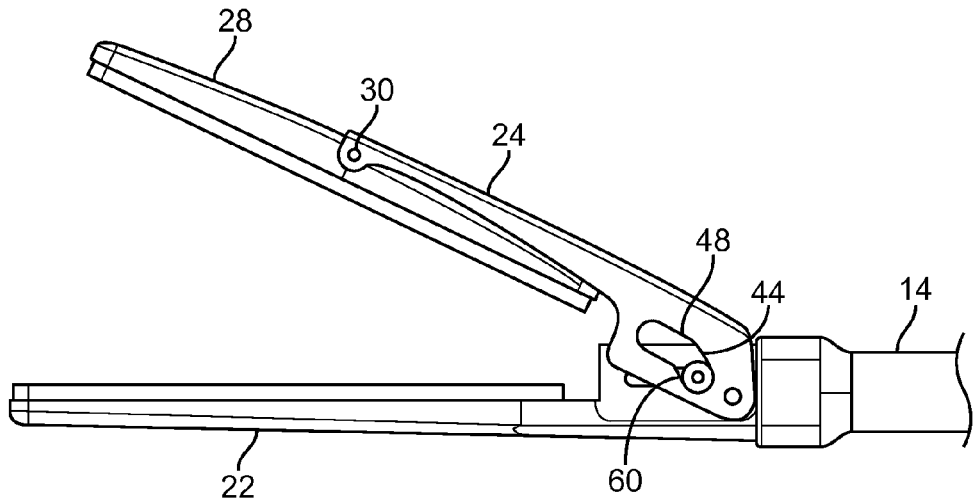
FIG. 11 is an enlarged side elevation of a clamp head in an open position.
Figure 12:
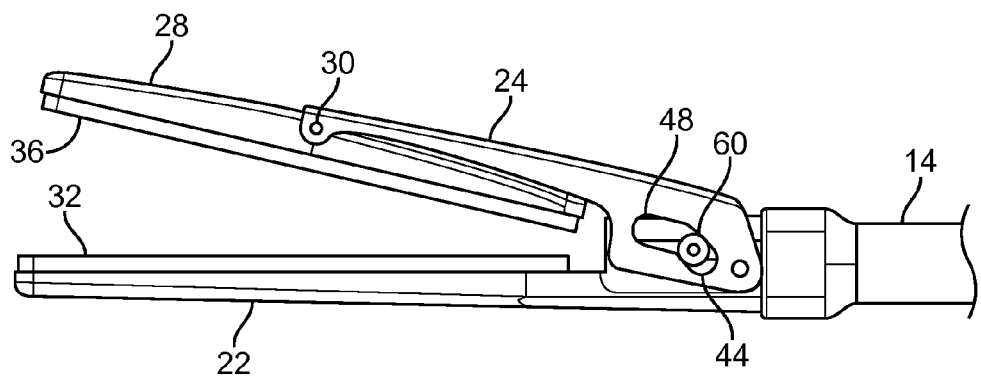
FIG. 12 is an enlarged side elevation of a clamp head in an intermediate position.
Figure 13:
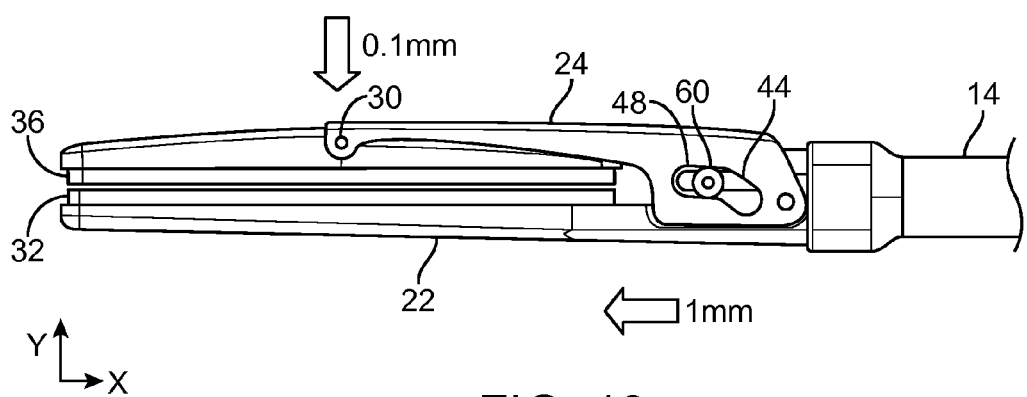
FIG. 13 is an enlarged side elevation of a clamp head in a closed position.

Structure for locking the jaws 22 and 28 in the closed position can be provided in different forms. In one aspect, the locking structure is a cam 40 and cam follower 60. The cam 40 has at least a first cam portion 44 and second cam portion 48 and is provided in the jaw actuator 24. The cam follower 60 moves in a linear fashion relative to the elongated handle 14. The first cam portion 44 is at a first angle relative to the direction of motion of the cam follower 60, and the second cam portion 48 is at a second angle relative to the direction of motion of the cam follower 60. As shown in FIGS. 11-13, movement of the cam follower 60 in the first, closing portion 44 of the cam 40 causes the jaw actuator 24 to close the jaw 28 relative to the jaw 22. Further movement of the cam follower 60 moves the cam follower 60 into the second, locking portion 48 of the cam 40 as shown in FIG. 13. This closes the jaw 28 and locks the jaw 28 in position relative to the jaw 22. The aorta will be firmly closed and locked between the jaw 22 and the jaw 28.

Figure 14:
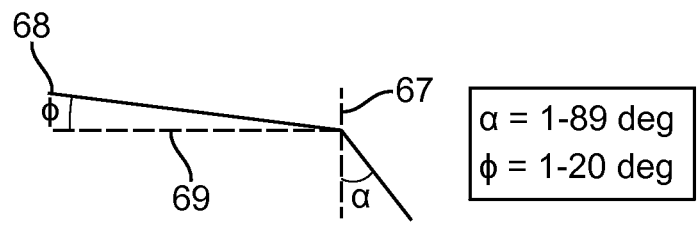
FIG. 14 is a diagram illustrating cam and cam follower angles.

There is shown in FIG. 14 a representation of an axis or path of motion 68 of the cam 40, both in the first cam portion 44 and in the second cam portion 48. The angle α between an axis 68 of the cam 40 in the first cam portion 44 and a perpendicular imaginary line 67 relative to the direction of motion of the cam follower 60 can be from 1 to 89° and any angle there between. The angle φ between the second cam portion 48 and an imaginary line 69 representing the direction of motion of the cam follower 60 can be any angle between 1 and 20°, such as 1, 2, 3, 4, 5, 6, 7, 8, 9, 10, 11, 12, 13, 14, 15, 16, 17, 18, 19 and 20°. The cam can be curved and can provide any mechanical advantage of between 1 and 20.

Figure 15:
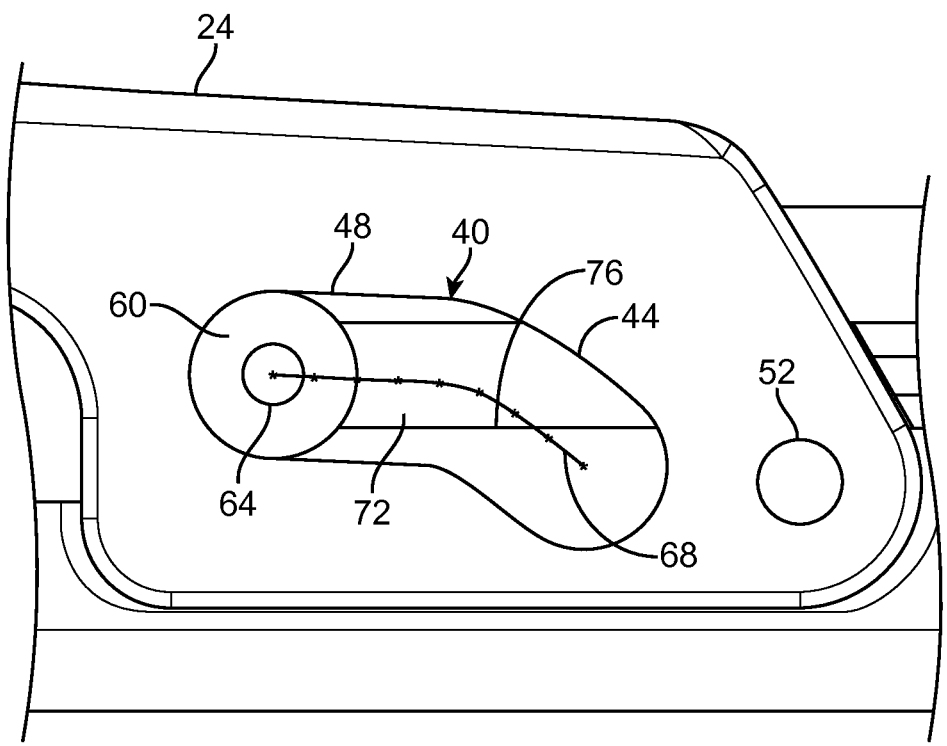
FIG. 15 is an enlarged side elevation of a cam and cam follower.

The cam follower 60 can be provided on cam follower pin 64 that is mounted to a cam shaft 72 as shown in FIG. 15. The cam shaft 72 can be mounted in a cam shaft recess 76. Advancement of the cam 40 causes the cam follower 60 to contact the surfaces of the cam 40 such that the cam 40 and actuator 24 are caused to move so as to close the jaw 28 relative to the jaw 22. Any suitable mechanism for opening and closing the jaws can be utilized.

Figure 17:
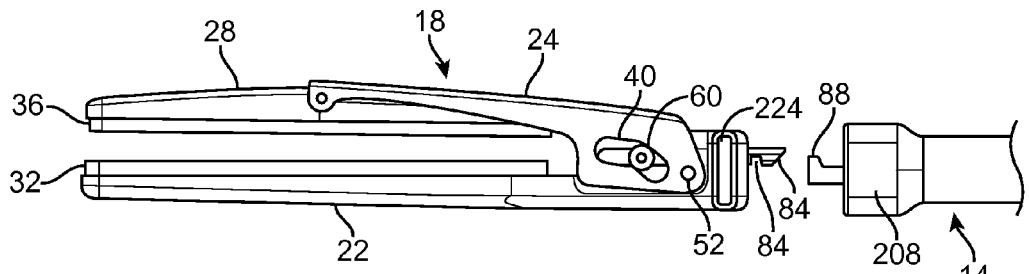
FIG. 17 is a side elevation illustrating a detached clamp head in an intermediate position.
Figure 18:
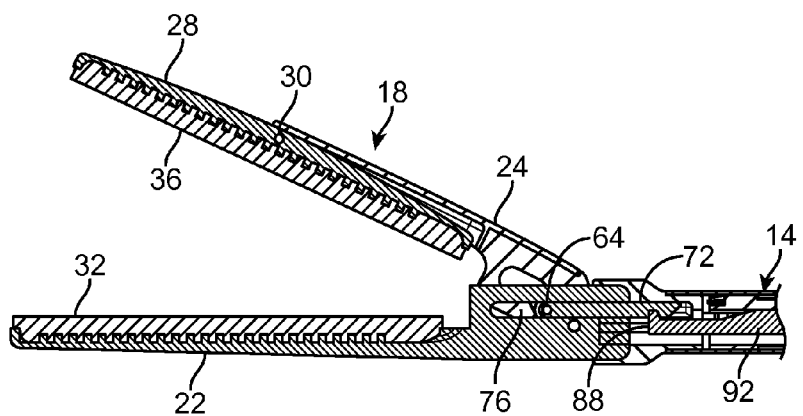
FIG. 18 is a cross-section of a clamp head in an open position.
Figure 19:
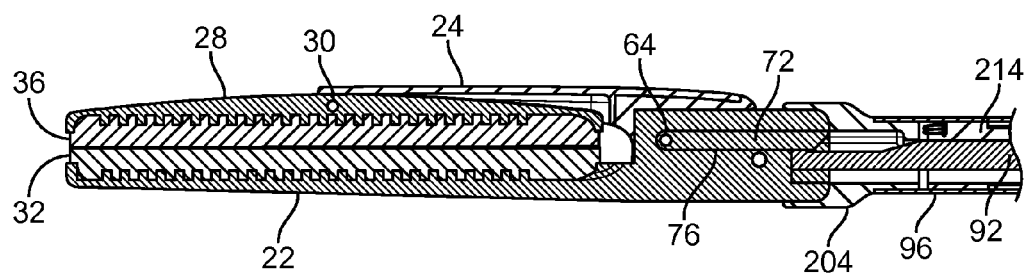
FIG. 19 is a cross-section of a clamp head in a closed position.
Figure 31:
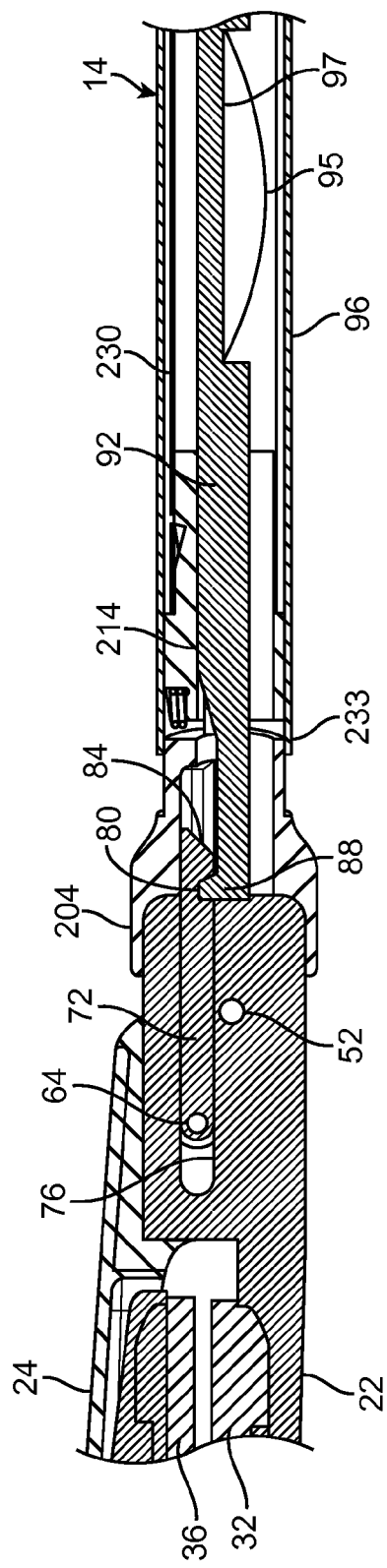
FIG. 31 is a cross-section of a clamp head grasper assembly in an open position.
Figure 32:
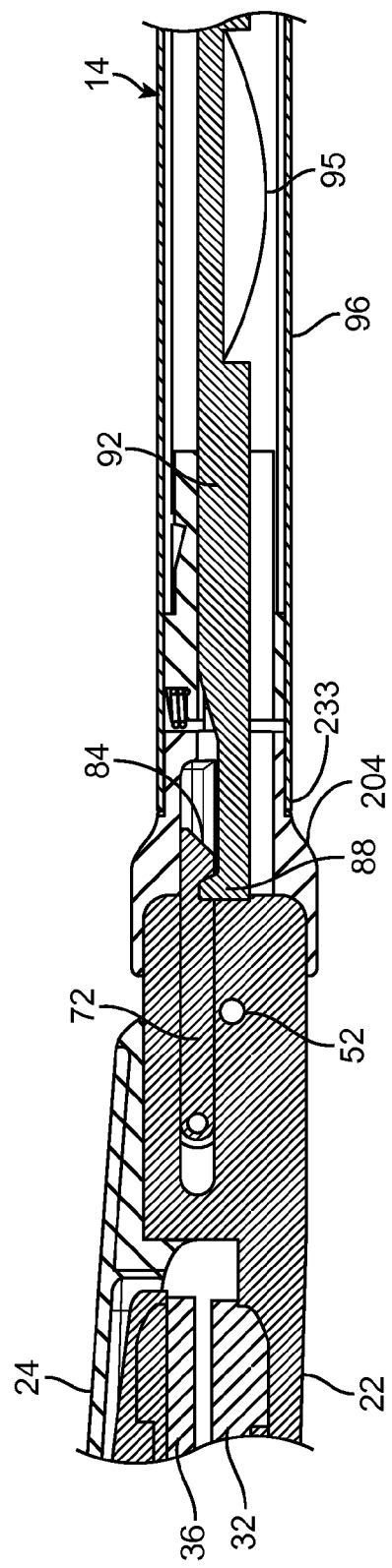
FIG. 32 is a cross section of a clamp head grasper assembly in a closed position.

The cam shaft 72 can be engaged to a jaw drive shaft 92 in the elongated handle 14, as shown in FIG. 18. The cam shaft 72 can have a recess 80 for receiving a protrusion 88 at the distal end of the jaw drive shaft 92 (FIG. 17 and FIGS. 31-32). The proximal end 84 of the cam shaft 72 can be inclined so as to direct the protrusion 88 into the recess 80. A biasing such as leaf spring 95 can be provided and a spring seat 97 to urge the jaw drive shaft 92 and protrusion 88 into the recess 80 to securely engage the jaw drive shaft 92 to the cam shaft 72 (FIG. 32). In that manner, axial movement of the jaw drive shaft 92 will cause similar movement of the cam shaft 72 and corresponding movement of the cam follower pin 64 and cam follower 60. A tubular housing 96 can be concentrically positioned so as to enclose the jaw drive shaft 92 and leaf spring 95.

Figure 5:
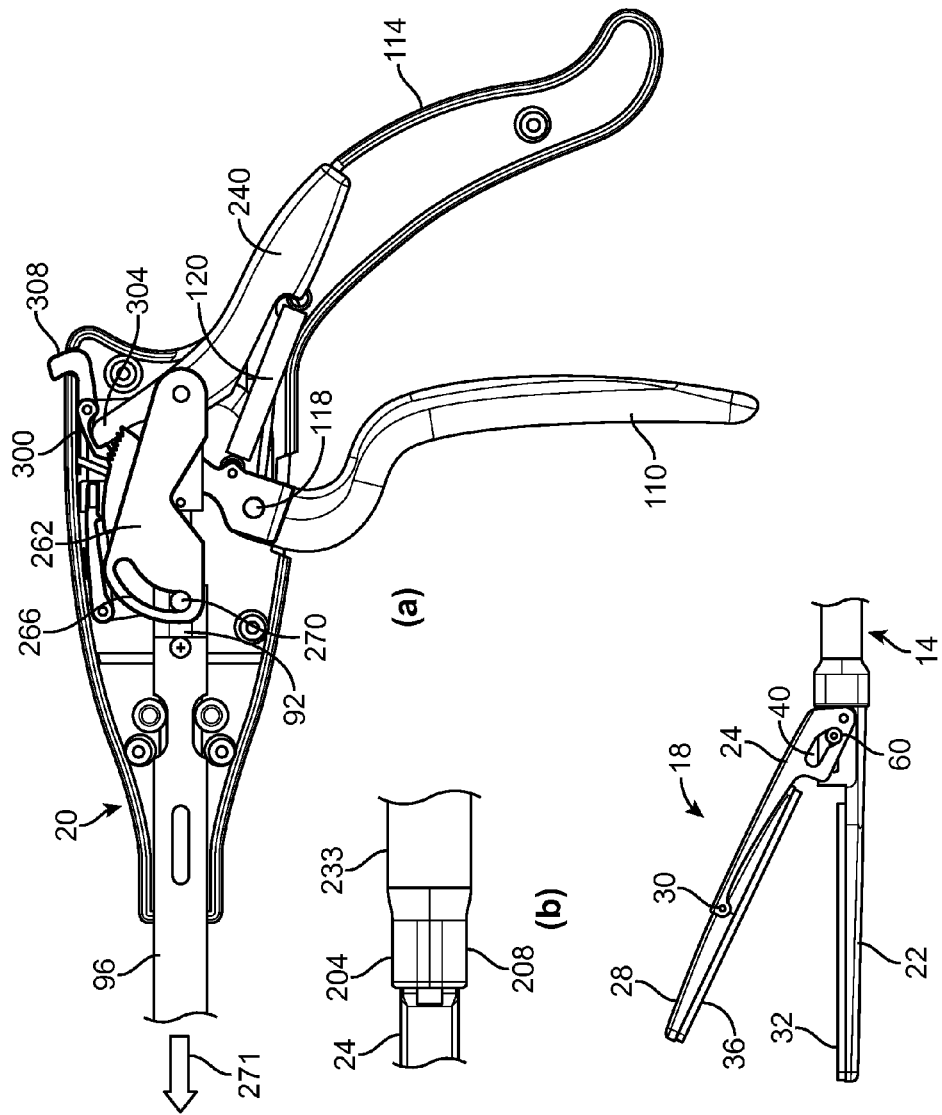
FIG. 5 is a) a cross-section of a handle grip assembly; b) a plan view of a clamp head engagement assembly; and c) a side elevation of a clamp head, in a first, open position.
Figure 20:
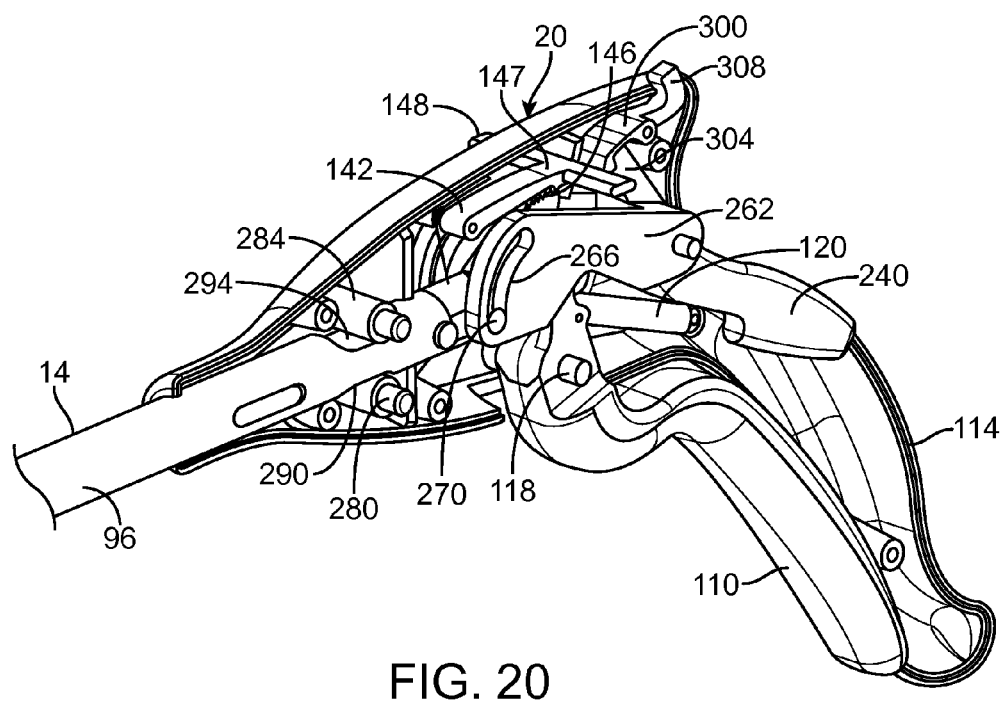
FIG. 20 is a perspective view of a handle grip assembly having a portion of the housing removed to reveal internal features.
Figure 21:
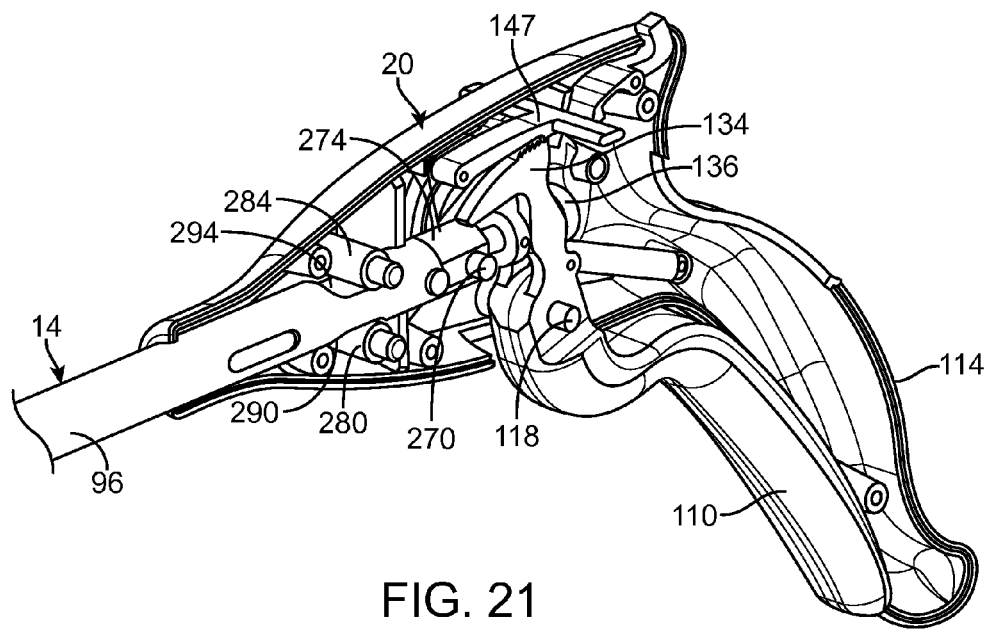
FIG. 21 is a perspective view of a handle grip assembly having a portion of the housing and some parts removed to reveal internal features.
Figure 22:
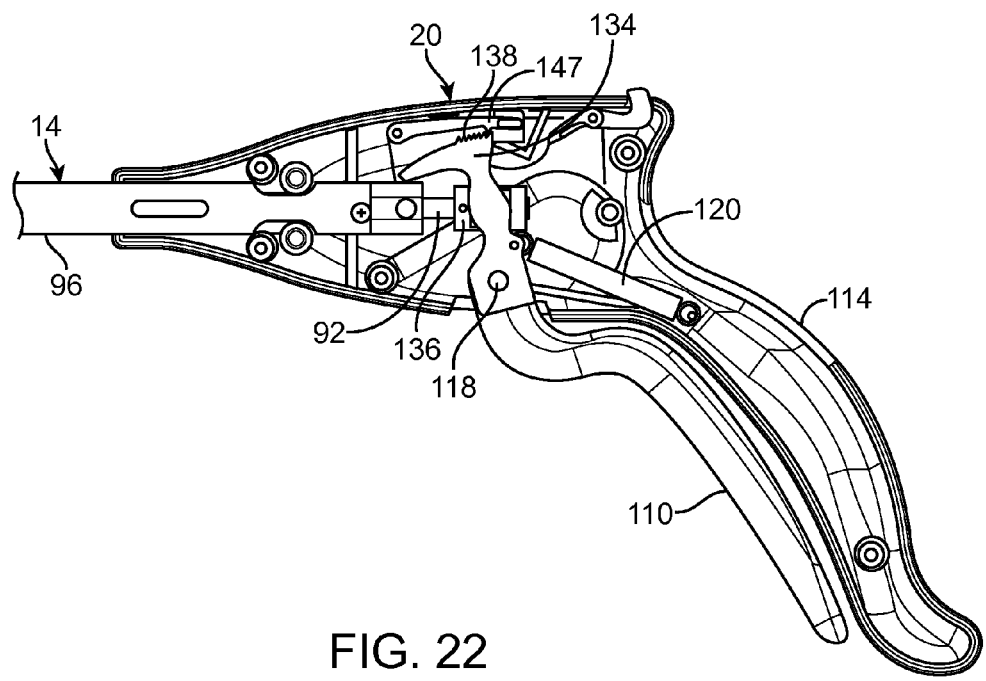
FIG. 22 is a side elevation.

The mechanism by which the jaw drive shaft 92 is moved to actuate the cam shaft 72 can vary and can be mechanical or electrical. In the embodiment shown particularly in FIGS. 5-6, the jaw drive shaft 92 is moved by operation of a trigger 110 which can be operated with the hand around a grip 114 provided in the handle 20 (FIGS. 20-22). The trigger 110 can be pivotally mounted about a pin 118 and can be biased by a suitable biasing such as spring 120 to the open position. The trigger 110 is operatively connected to a lever arm 134. The biasing spring 120 acts against the lever arm 134 to cause movement of the lever arm 134 proximally, and rotation of the trigger 110 away from the grip 114 to an open position as shown in FIG. 5(a). The lever arm 134 is mounted within a collar 136. The collar 136 is connected to a proximal end of the jaw drive shaft 92 (FIG. 22). Proximal movement of the trigger 110 by squeezing will cause forward rotation of the lever arm 134 to move the collar 136 and jaw drive shaft 92 distally. This will cause distal movement of the cam shaft 72, which will operate to move the cam follower 60 distally and close the jaw actuator 24 and jaw 28.

Structure can be provided for securing the jaws in the closed position. Ratchet teeth 138 can be provided on the lever arm 134 to engage teeth 146 on a ratchet pawl 147 that is provided on a ratchet arm 142 as shown in FIG. 20. The ratchet arm 142 and pawl 147 holds the lever arm 134 in the closed position. Extension 148 extending out of the housing 20 can be lifted to disengage the ratchet teeth 146 on ratchet pawl 147 from the ratchet teeth 138 on the lever arm 134 to release the lever arm 134 (FIG. 20).

Figure 29:
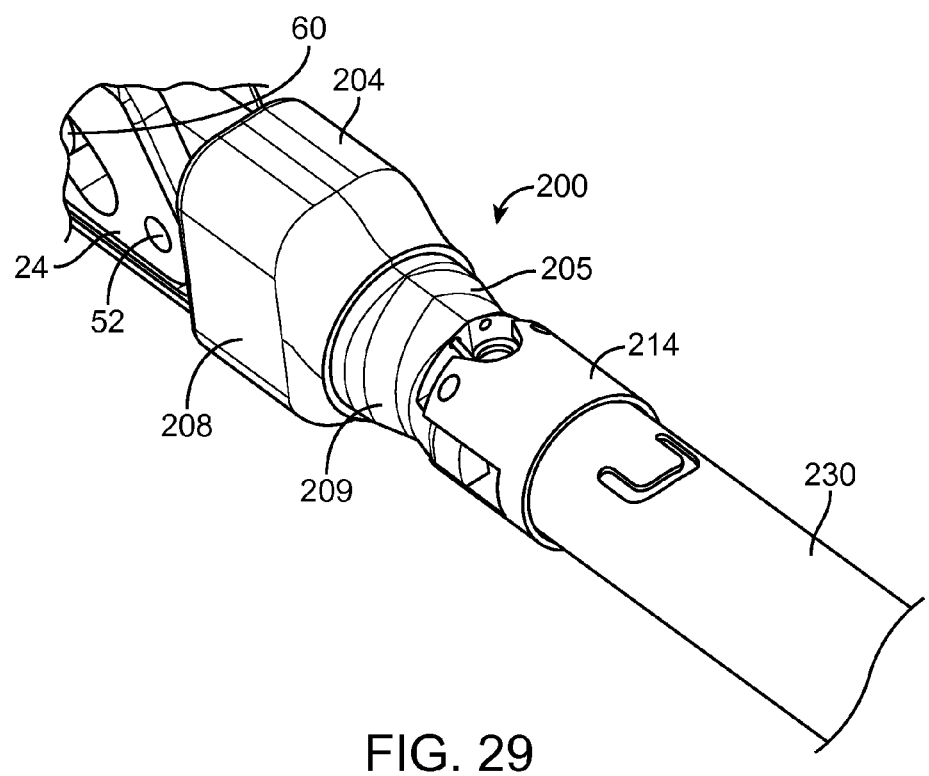
FIG. 29 is an enlarged perspective of a clamp head grasper assembly in a closed position.
Figure 30:
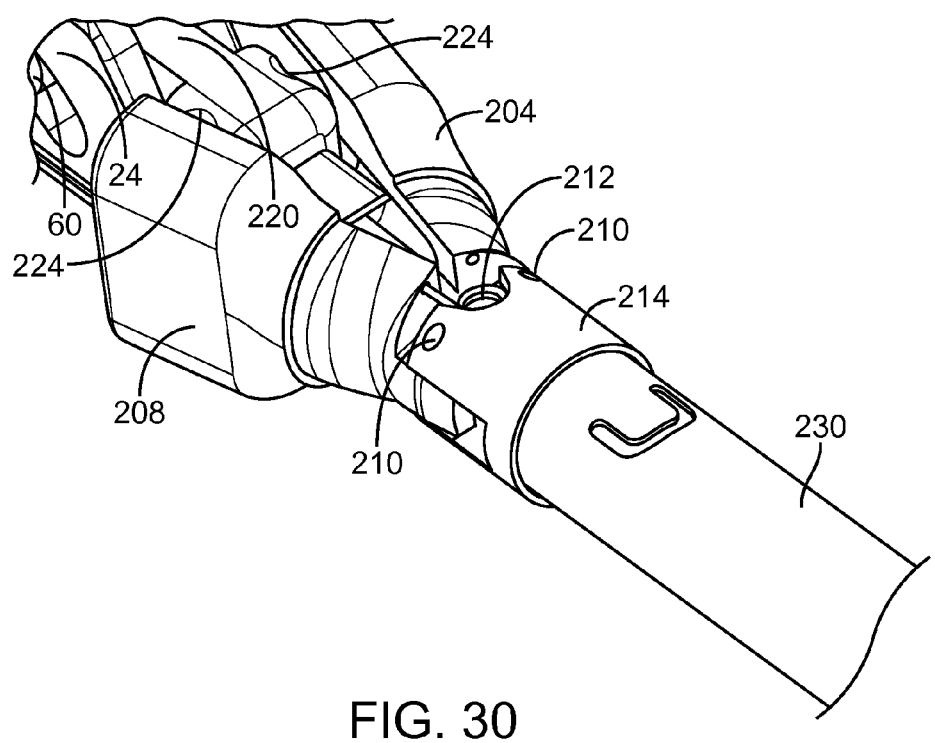
FIG. 30 is an enlarged perspective of a clamp head grasper assembly in an open position.
Figure 33:
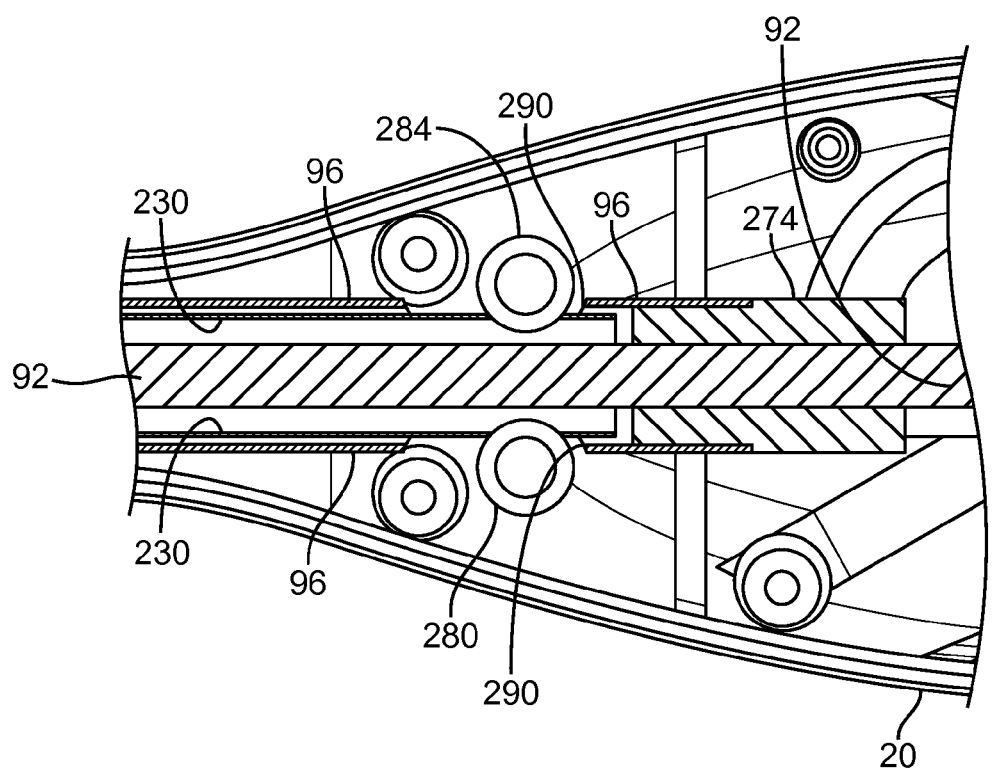
FIG. 33 is an enlarged cross-section of a proximal end of the elongated shaft.

The manner in which the clamp head 18 is detached and engaged from the elongated handle 14 can vary, and can be mechanical or electrical. One sample engagement mechanism 200 is shown particularly in FIGS. 29-30 and elsewhere in the drawings. In one aspect, graspers 204 and 208 are provided at a distal end of the elongated handle 14 (FIGS. 29-30). The graspers 204 and 208 are pivotally mounted to a seat 214 about pivot pins 210. The seat 214 is mounted to a sleeve 230 which is concentric to the jaw drive shaft 92 and supported by posts 280 and 284 which are positioned in corresponding seats 290, 294 in the housing 96 (FIG. 33). The housing 96 is concentric to and laterally outward from the sleeve 230. A biasing such as spring 212 is provided to open the graspers 204, 208 to the position shown in FIG. 30.

The housing 96 is used to actuate the graspers 204, 208 as shown in FIGS. 5-10 and FIGS. 29-32. In a first axial position, the housing 96 is in the position shown in FIG. 31 in which the graspers 204, 208 are in the open position shown in FIG. 30. As the housing 96 is moved distally over the seat 214 (FIG. 32), the leading edge 233 of the housing 96 will be forced over wedge surfaces 205 and 209 which will act to drive these surfaces laterally inward to close the graspers 204, 208.

Figure 16:
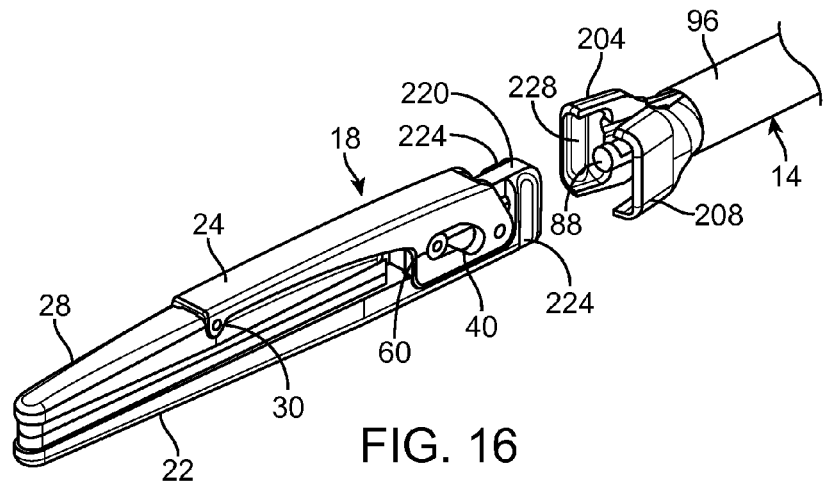
FIG. 16 is an enlarged perspective illustrating a detached clamp head in a closed position.

The graspers 204, 208 have engagement structure which cooperate with engagement structure on the clamp head 18 to detachably engage the elongated handle 14 to the clamp head 18. In one aspect, this structure comprises cooperating engagement protrusions and receptacles. A clamp head member 220 can have receptacles 224 as shown in FIGS. 16-17. Inside surfaces of the graspers 204, 208 can have protrusions 228 for engaging the receptacles 224 when the graspers 204, 208 are closed around the clamp head member 220.

Figure 6:
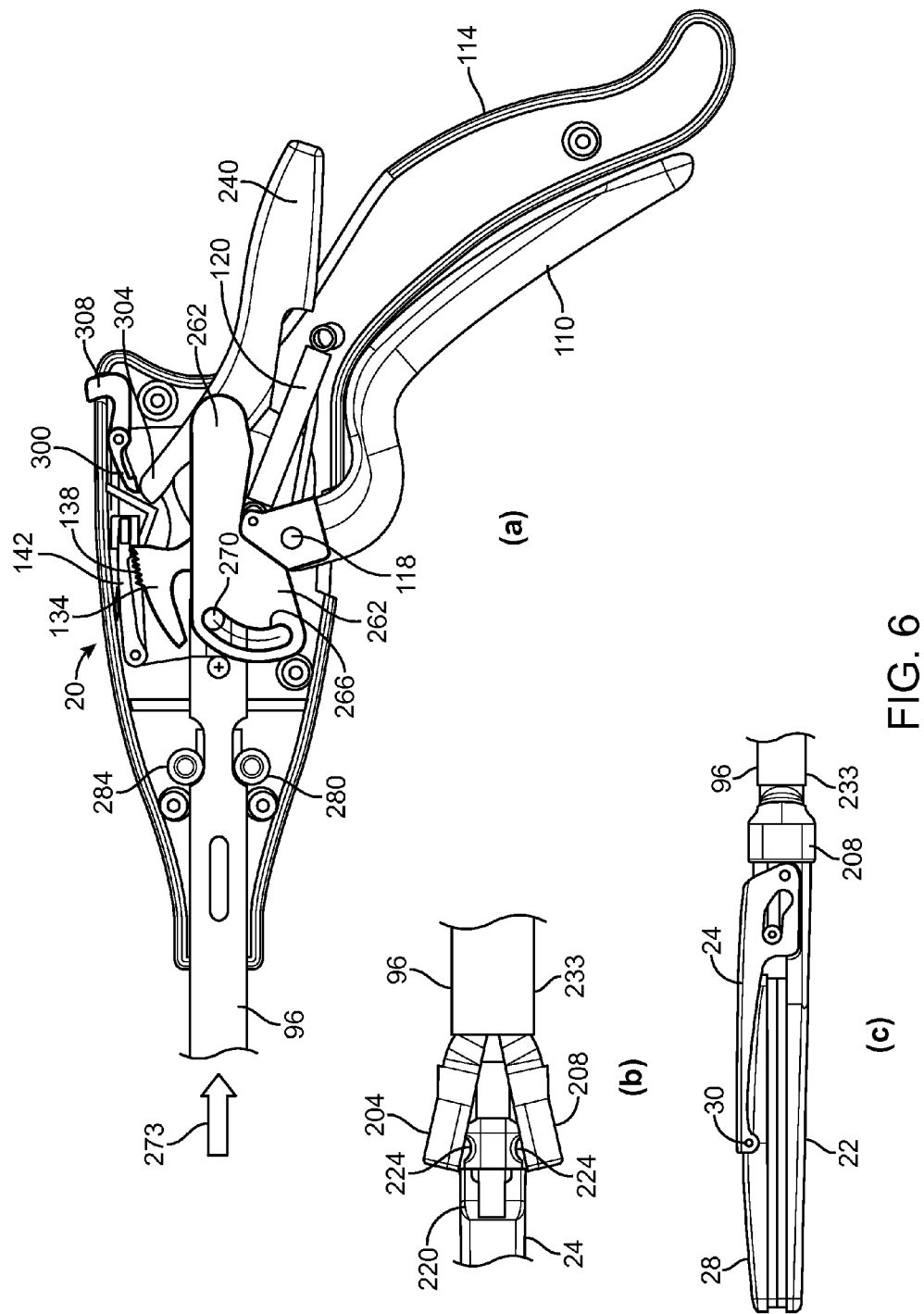
FIG. 6 is a) a cross-section of a handle grip assembly; b) a plan view of a clamp head engagement assembly; and c) a side elevation of a clamp head, in a second, closed position.
Figure 7:
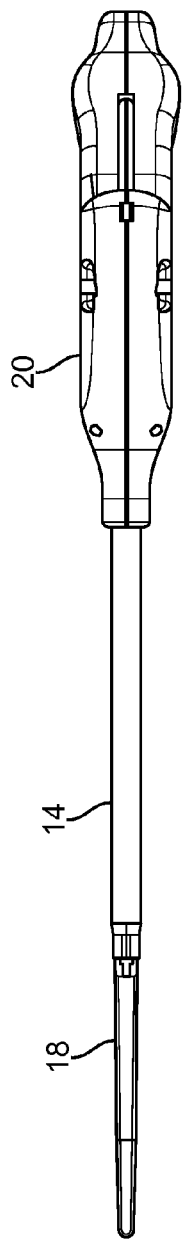
FIG. 7 is a plan view of an aortic cross clamp with graspers for the clamp head in a first position.
Figure 8:
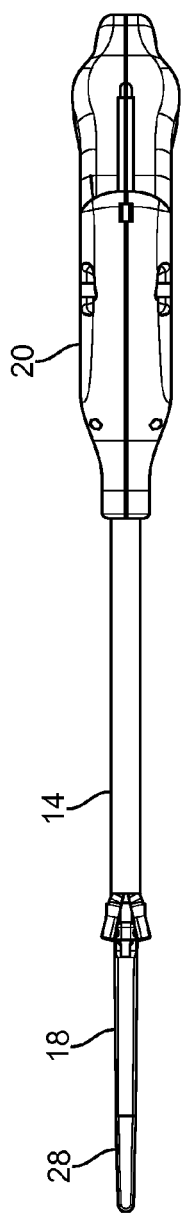
FIG. 8 is a plan view of an aortic cross clamp with graspers for the clamp head in a second position.
Figure 9:
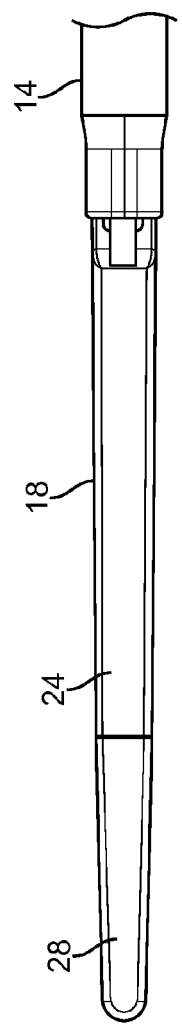
FIG. 9 is an enlarged view of a clamp head and graspers in the first position.
Figure 10:
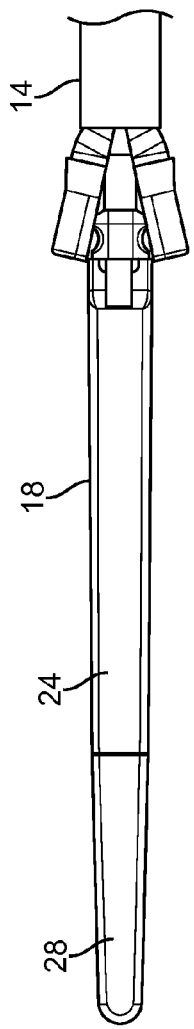
FIG. 10 is an enlarged plan view of the clamp head and graspers in a second position.

Axial movement of the housing 96 can be produced by any suitable mechanism, including mechanical and electrical mechanisms. In the embodiment shown, a grasper actuating lever 240 is provided in the handle grip housing 20. The grasper actuating lever 240 is connected to a cam member 262 having a cam 266 (FIG. 20). A cam follower 270 is positioned in the cam 266 and connected to a cam follower support 274 (FIG. 21). The cam follower support 274 is connected to the housing 96, such that axial movement of the cam follower support 274 will cause axial movement of the housing 96 (FIGS. 21 and 33). As shown in FIGS. 5-6 movement of the grasper actuating lever 240 causes rotational movement of the cam member 262 between the position shown in FIG. 5 and the position shown in FIG. 6. In the closed position shown in FIG. 5, the cam member 262 and cam 266 is moved to a position such that the cam follower 270 is at a bottom portion of the cam 266. The cam follower 270, cam follower support 274 and housing 96 are moved axially and distally as shown by the arrow 271 (FIG. 5). In the open position shown in FIG. 6, the grasper actuating lever 240 is moved to a position where the cam member 262 and cam 266 are rotated counterclockwise such that the cam follower 270 is moved to a position at a top portion of the cam 266. The cam follower 270, cam follower support 274 and housing 96 are driven axially and proximally as shown by the arrow 273 (FIG. 6). The leading edge 233 of the housing 96 is moved into the position shown in FIG. 6(c) causing the graspers 204, 208 to open under the action of biasing spring 212. The grasper actuating lever 240 can be biased by a suitable biasing structure such as a spring.

A locking portion 304 of the grasper actuating lever 240 can be provided to engage a locking arm 300. The locking arm 300 retains the grasper actuating lever 240 in the closed position shown in FIG. 5. A release tab 308 is connected to the locking arm 300 such that downward pressure on the release tab 308 will cause the locking arm 300 to pivot out of engagement with the locking portion 304 of the grasper actuating lever 240 to permit the grasper actuating lever 240 return under the action of the biasing spring to the open position shown in FIG. 6.

The aortic cross clamp can have dimensions which are suited for minimally invasive surgical techniques. In one aspect, the clamp head can be passed through a port or 4 mm incision and can have a maximum dimension of 1 mm, 2 mm, 3 mm, 4 mm, 5 mm, 6 mm, 7 mm, 8 mm, 8 mm, 9 mm, 10 mm, 11 mm, 12 mm, 13 mm, 14 mm, or 15 mm.

A method of clamping the aorta according to the invention includes the steps of providing an aortic cross clamp having an elongated handle, a clamp head, the clamp head having opposing jaws having open and closed positions, at least one of the jaws being pivotally mounted to a jaw actuator so as to be pivotal relative to the opposing jaw and about an axis distanced from the opposing jaw, and a locking mechanism for locking the jaws in the closed position, and a jaw drive mechanism operable through the elongated handle for moving the jaws between the open and closed positions. The method further includes the step of closing the jaws about an aorta while permitting the pivotally mounted jaw to pivot upon contact with the aorta. The method can also comprise the step of detaching the clamp head from the handle after the jaws have been closed about the aorta. The pivoting movement of the jaw reduces the likelihood of pinching or scissoring to the proximal aspect of the vessel engaged within the jaws, the side that is closest to the jaw hinge, which further minimizes the potential for excessive bruising or damage to the aorta or other vessel being engaged. Detachment of the clamp head minimizes the obstructive element presented by the handle and removes the delivery mechanism from the operative site, thereby enhancing access to and visualization of the target site when operating in a minimally invasive setting presented by a small incision or port. The small dimension of the clamp head minimizes the necessary dimension of the access site necessary for delivery of the clamp head to the target site, which complements minimally invasive surgical methods.

This invention can be embodied in other forms without departing from the spirit or essential attributes thereof. Reference should be made to the following claims to determine the scope of the invention.

We claim:

1. An aortic cross clamp, comprising:
a locking mechanism for locking and retaining tissue engaging structures in a closed position, a clamp head having opposing jaws having proximal and distal ends and movable between open and closed positions, at least one of the jaws being a pivot jaw pivotally mounted to a pivot jaw actuator arm, the pivot jaw actuator arm being connected to the opposing jaw through a first, proximal pivot axis, the pivot jaw actuator arm and the opposing jaw being movable about the proximal pivot axis to define the open and closed positions, the pivot jaw being pivotally mounted to the pivot jaw actuator arm about a second, medial pivot axis between the proximal and distal ends of the pivot jaw, the medial pivot axis being distanced distally from the proximal pivot axis, the proximal and distal ends of the pivot jaw being free to pivot independently of engagement with another structure, and the pivot jaw being independently pivotal relative to the opposing jaw about the medial pivot axis, the clamp head further comprising a first jaw drive mechanism for moving the jaws between the open and closed positions, a second jaw drive mechanism detachably connectable to the first jaw drive mechanism in the clamp head and operable for moving the jaws between the open and closed positions, wherein the locking mechanism is provided in the clamp head and movable between locked and unlocked positions, wherein the clamp head and an elongated handle have cooperating engagement structure operable from the handle for detachably engaging the clamp head to the distal end of the elongated handle, and cooperating engagement structure for detachably engaging the first jaw drive mechanism to the second jaw drive mechanism, the locking mechanism when placed in the locked position remaining in the locked position when the clamp head is detached from the handle to lock the clamp head in the closed position.

2. The aortic cross clamp of claim 1, wherein the elongated handle comprises an elongated sliding shaft having proximal and distal ends, the second jaw drive mechanism being operable through the elongated sliding shaft of the handle for moving the first jaw drive mechanism and thereby the jaws between the open and closed positions; wherein the locking mechanism is actuated through sliding movement of the elongated sliding shaft of the handle to move the locking mechanism between the locked and unlocked positions.

3. The aortic cross clamp of claim 1, wherein the locking mechanism comprises a cam and a cam follower.

4. The aortic cross clamp of claim 3, wherein the cam is curved and has a mechanical advantage of between 1 and 20.

5. The aortic cross clamp of claim 4, wherein the clamp head has a long axis and the cam has first and second cam portions, the first cam portion making an angle of between 1-89 with the long axis and the second cam portion making an angle of between 1-20 with the long axis.

6. The aortic cross clamp of claim 3, wherein the cam follower is connected to a cam shaft.

7. The aortic cross clamp of claim 6, wherein the jaw drive mechanism comprises a jaw drive shaft in the elongated handle, the jaw drive shaft being connectable to cooperating structure on the cam shaft to move the jaws between the open and closed positions.

8. The aortic cross clamp of claim 7, wherein the cam shaft has a proximal end and a distal end, the distal end being connected to the cam follower, the proximal end having structure for detachably engaging the jaw drive shaft.

9. The aortic cross clamp of claim 8, wherein the elongated handle comprises a tubular housing, and the jaw drive shaft is provided within the housing.

10. The aortic cross clamp of claim 8, wherein the elongated handle is attached to a handle grip housing, and the jaw drive mechanism further comprises a jaw drive cam follower connected to the jaw drive shaft, and a jaw drive cam is mounted to the handle grip housing, movement of the jaw drive cam causing movement of the jaw drive cam follower and the jaw drive shaft so as to move the jaw drive shaft proximally or distally and move the jaws between the open and closed positions.

11. The aortic cross clamp of claim 10, further comprising a trigger for causing movement of the jaw drive cam.

12. The aortic cross clamp of claim 11, further comprising a biasing for the trigger and a ratchet for securing the trigger in a position against the action of the biasing.

13. The aortic cross clamp of claim 2, wherein the cooperating engagement structure comprises opposing graspers pivotally mounted to the elongated handle.

14. The aortic cross clamp of claim 13, wherein the graspers are biased to an open position and a grasper drive member is operable to move the graspers against the biasing to a closed position.

15. The aortic cross clamp of claim 14, wherein the grasper drive member is tubular.

16. The aortic cross clamp of claim 15, further comprising a grasper actuating lever, movement of the grasper actuating lever being operable to move the grasper drive member and the graspers between the open and closed positions.

17. The aortic cross clamp of claim 1, wherein the jaws comprise an engagement pad.

18. The aortic cross clamp of claim 1, wherein the pivot jaw is pivotally mounted to the pivot jaw actuator arm by a pivot pin aligned with the medial pivot axis.

* * * * *